United States Patent
Weiguo

(10) Patent No.: US 8,973,528 B2
(45) Date of Patent: Mar. 10, 2015

(54) SPLIT FEED DISTRIBUTOR WITH FEED SUPPLIED FROM BELOW AND THROWN CIRCUMFERENTIALLY

(76) Inventor: Wu Weiguo, Zhejiang (CN)

(*) Notice: Subject to any disclaimer, the term of this patent is extended or adjusted under 35 U.S.C. 154(b) by 0 days.

(21) Appl. No.: 13/504,104

(22) PCT Filed: May 25, 2011

(86) PCT No.: PCT/CN2011/074648
§ 371 (c)(1),
(2), (4) Date: Apr. 25, 2012

(87) PCT Pub. No.: WO2012/062099
PCT Pub. Date: May 18, 2012

(65) Prior Publication Data
US 2013/0215414 A1 Aug. 22, 2013

(30) Foreign Application Priority Data
Nov. 13, 2010 (CN) .......................... 2010 1 0555223

(51) Int. Cl.
*A01K 39/014* (2006.01)
*G01N 21/47* (2006.01)
*A01K 61/02* (2006.01)
*G01N 21/59* (2006.01)
*G01N 21/64* (2006.01)

(52) U.S. Cl.
CPC ................ *G01N 21/47* (2013.01); *A01K 61/02* (2013.01); *G01N 21/59* (2013.01); *G01N 21/64* (2013.01)
USPC ..................................... 119/57.91; 119/57.92

(58) Field of Classification Search
USPC .......... 119/57.91, 51.01, 51.04, 51.11, 51.12, 119/51.13, 51.14, 51.15, 57.92, 57.1, 57.2, 119/61.2, 210, 212, 230, 242; 239/650, 239/668, 681, 684, 683, 688, 689; 221/258, 221/277; 222/251, 410, 333
See application file for complete search history.

(56) References Cited

U.S. PATENT DOCUMENTS

| | | | | |
|---|---|---|---|---|
| 4,967,697 | A * | 11/1990 | Lau ............................ | 119/51.04 |
| 5,975,021 | A * | 11/1999 | Shingleton et al. ........... | 119/230 |
| 6,016,767 | A * | 1/2000 | Kyrkjebø ................... | 119/51.04 |
| 7,222,583 | B2 * | 5/2007 | Foster et al. ............... | 119/57.91 |
| 7,798,098 | B1 * | 9/2010 | Patterson ................... | 119/51.11 |
| 8,573,156 | B2 * | 11/2013 | Gates .............................. | 119/53 |
| 8,631,764 | B2 * | 1/2014 | Quiring et al. ............. | 119/57.91 |
| 2002/0185075 | A1 * | 12/2002 | Glover et al. .............. | 119/57.91 |
| 2005/0241588 | A1 * | 11/2005 | Foster ........................ | 119/57.91 |
| 2008/0029033 | A1 * | 2/2008 | Harrison et al. ........... | 119/51.04 |

* cited by examiner

*Primary Examiner* — Trinh Nguyen
(74) *Attorney, Agent, or Firm* — John Alumit

(57) ABSTRACT

A feed distributor used in fish ponds with feed supplied from below and thrown circumferentially comprises a feed-supplying mechanism, a feed-throwing mechanism and a feed-conveying mechanism by which feed supplied from said feed-supplying mechanism is delivered to said feed-throwing mechanism; the feed-supplying mechanism has a hopper which connects with a feed container above and a feed conveyor below. The feed-throwing mechanism has a launching disc with a sealed top, feed outlets in its circumference and a feed inlet below. The launching disc is disposed on a hollow shaft with an inner hole opposed to said feed inlet. The feed-throwing mechanism is disposed in pond and the feed supplying mechanism settles on a bank, feed is sucked into the feed-throwing disc and thrown circumferentially under negative pressure caused by rotation of the launching disc, and has a low crushing rate.

1 Claim, 11 Drawing Sheets

SPLIT FEED DISTRIBUTOR WITH FEED SUPPLIED FROM BELOW AND THROWN CIRCUMFERENTIALLY

CROSS-REFERENCE TO RELATED APPLICATION

This application is a national stage application that claims the benefit of PCT application no. PCT/CN2011/074648 filed on May 25, 2011 (not yet published). The earliest priority date claimed is Nov. 13, 2010.

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

This present invention relates generally to a feed distributor in the field of mechanical technology in aquaculture. More particularly, this invention relates to a split feed distributor with feed supplied from below and thrown circumferentially in fish ponds or the like.

A feed distributor is necessary for feeding in aquaculture. Usually, the feed distributor is installed on the bank of fish ponds, with feed supplied from the top and thrown in only one direction, or in two directions as seen in Chinese Patent Application CN200620165358.0. The feed distributor therein has two electric motors which complicates the configuration of the machine, and a limited coverage for feed-throwing, which is unsuitable for feeding shrimp, prawn, lobster, etc. It is well known that shrimp, prawn, lobster, and other crustaceans only swim and eat in small areas around themselves. When a lot of them gather together in a small area, it results in overpopulation which is harmful to them as some are unable to obtain an adequate amount of food. As a result, most feeding must be done by hand. In Chinese Patent Application CN200920040435.3, the feed distributor therein throws feed circumferentially. However, it is necessary for a feed conveyer to have a vibration mechanism and 0-15° altitude difference from the launching disc. In this way, feed could be supplied to said launching disc and then thrown. In addition, the supporting pole for fixing the electric motor would block the feed that is thrown and crush it.

SUMMARY OF THE INVENTION

The present invention provides a split feed distributor with feed supplied from below and thrown circumferentially to overcome the above-mentioned problems in aquaculture.

According to the invention, the feed distributor with feed supplied from below and thrown circumferentially comprises: a feed-supplying mechanism; a feed-throwing mechanism for throwing feed from said feed-supplying mechanism, which has a launching disc with a sealed top, feed outlets in its circumference and a feed inlet below which settles on a hollow shaft whose inner hole is opposed to said feed inlet below; a feed-conveying mechanism, by which feed supplied from said feed-supplying mechanism is conveyed to said feed-throwing mechanism.

Said launching disc rotates with said hollow shaft by transmission means; alternatively, said launching disc can rotate by an electric motor with a hollow spindle which forms said hollow shaft; a discharge tube, which does not rotate and connects with a conveying pipe below, is disposed in the inner hole of said hollow spindle; alternatively, said hollow shaft can be fixedly mounted on a base for supporting a rotor with a bearing outside; and said rotor is driven with power by transmission means; alternatively, said rotor can be the rotor from an electric motor with a hollow spindle which forms said hollow shaft; and said hollow spindle connects with a conveying pipe below.

A sealed means settles between said discharge tube and hollow shaft to prevent feed deposition; alternatively, a circular or spiral convex-concave structure can be disposed in the outer surface of said conveying pipe or inner surface of said hollow shaft to prevent feed deposition.

Said launching disc comprises an upper member and a lower member, and said lower member has a mounting plate and said feed inlet below; between said lower member and upper member, a guide plate for feed throwing is disposed evenly within the circumference of the lower and upper members in the radial direction outwards in line with a certain radius; a guide channel formed by the cavity between two said guide plates comprises: a diffusion type, with a bigger opening outside and a smaller opening inside in the radial direction; a contraction type, with a bigger opening inside and a smaller opening outside in the radial direction; or, a balance type, with the same size of opening outside and opening inside in the radial direction; alternatively, said launching disc can have a hollow case with a mounting plate and said feed inlet below and with guide tubes around the circumference of said launching disc; the guide channels or tubes are disposed horizontally at the same level or with the outside part a little higher than the inside part in a radial direction; and a cross-section of said guide tubes is rectangular, circular or in any form of curvature that could reduce air resistance.

Said lower member of said launching disc is made from a metal sheet subject to metal extrusion and connected with a flange of said hollow shaft; a cooling fan for an electric motor is disposed under said lower member or flange of said hollow shaft; said upper member and guide plates form a whole set made by injection molding or die casting; and the outside diameter of said upper member is bigger than that of said lower member; said upper member has an opening in the center, and said opening couples with a sealed member.

Said guide plates, channels or tubes of said launching disc are different in length, with a longer one and a shorter one disposed separately in a circumferential direction; alternatively, said guide channel is separated by an isolation plate into an upper channel and a lower channel in different lengths, and said isolation plate and guide plates are formed as a whole set by injection molding or die casting.

According to the invention, said feed-supplying mechanism has a cone-shaped hopper which connects with a feed container upwards and a feed conveyer below adjustable in feeding rate and interval time. The side walls of the cover for said feed container correspondingly engages the side plates of said feed container, and one of the side walls pivots with a side plate of said container and the opposite side wall is equipped with an iron or magnet pad which correspondingly engages a magnet or iron pad in the side plate of said container to lock said cover; in addition, and alternatively, the configuration of said feed conveyer can be as follows: said cone-shaped hopper connects with a discharge nozzle below, and a feed conveyor is disposed at the bottom opening of said hopper within said discharge nozzle; said feed conveyor has a dustpan that couples with the lower part of said opening; the back wall of said dustpan pivots outwardly with an end of a lever, and the other end of said lever connects with the back wall of said hopper; a bearing with an eccentric sleeve mounted in its inner ring is disposed on a bearing support in the bottom of said dustpan, and a feed electric motor whose spindle connects with said eccentric sleeve mounts fixedly below said hopper, and said discharge nozzle connects with a charge opening of said feed-conveying mechanism; alternatively, the configuration of said feed conveyer can be as follows: said cone-shaped hopper connects with a discharge nozzle below, and the end of said discharge nozzle connects with the charge opening of said feed-conveying mechanism; in addition, or alternatively, the configuration for the adjustment in the feeding rate of said feed conveyer can be: a rotatable door which could block said dustpan pivots to the front wall of said hopper, and said rotatable door has an adjusting lever with a regulator outside, and said feeding rate could be adjusted by rotation of said regulator fixed anywhere as needed by bolts or the like.

Said feed-conveying mechanism comprises only a conveying pipe which connects with said feed-supplying mechanism at one end and said feed-throwing mechanism at the other end. Alternatively, in the middle of said conveying pipe, said feed-conveying mechanism also has a sucking device with a filter and a valve, and said sucking device connects with said conveying pipe. Alternatively, an air blower is disposed outside of said conveying pipe in the direction from discharge opening to charge opening; alternatively, an auger is disposed inside said charge opening of said conveying pipe; alternatively, an auger is disposed inside of said charge opening of said conveying pipe and an air blower is disposed outside of said conveying pipe.

Said conveying pipe is made from flexible hose with a support frame, which has a charge opening connecting to said feed-supplying mechanism and a discharge opening connects to said hollow shaft or said discharge tube and a central part floats in the water.

Said feed-throwing mechanism has a support below which could be a floater, a stake, a base or the like.

Compared with the prior art, the present invention has the following advantages: feed is conveyed by negative pressure in the conveying pipe generated by rotation of the launching disc and thrown circumferentially without any blocking, which in turn contributes to a low crushing rate, a wide distributing coverage and an even distribution. The feeding rate could be adjusted so that feed could be distributed fast or slowly; in a slow distribution mode, feed thrown could be eaten up in time by fish, shrimp or the like, which in turn avoids waste and negative effects caused by the remaining feed. Under the sucking force caused by the rotation of said launching disc, feed is sucked upwards from the conveying pipe floating in the water into the launching disc, which is contrary to the tendency of the feed to move downwards over the launching disc. The feed-throwing distance relates to the linear velocity of the launching disc. With the speeding up or slowing down of said launching disc, force by negative gas flow and centrifugal force come up or down correspondingly. As usual, the suitable distance from the feed-throwing mechanism to the feed-supplying mechanism depends on the size of the pond. For example, a pond that is 60 meters in width, having the feed-throwing mechanism disposed in the center of the pond should be 30 meters away from the bank; the linear velocity of the launching disc could be adjusted so that feed could be thrown at a distance about 28-29 meters, and said launching disc should be about 1-2 meters over the water. In this case, about 40 meters of conveying pipe is needed for normal performance of the feed distributor of this invention. With an auxiliary feeding device, feed could be delivered directly from a warehouse. With the application of the present invention, throwing feed by hand could be avoided, which reduces workload and improves feeding efficiency.

Figure 1:
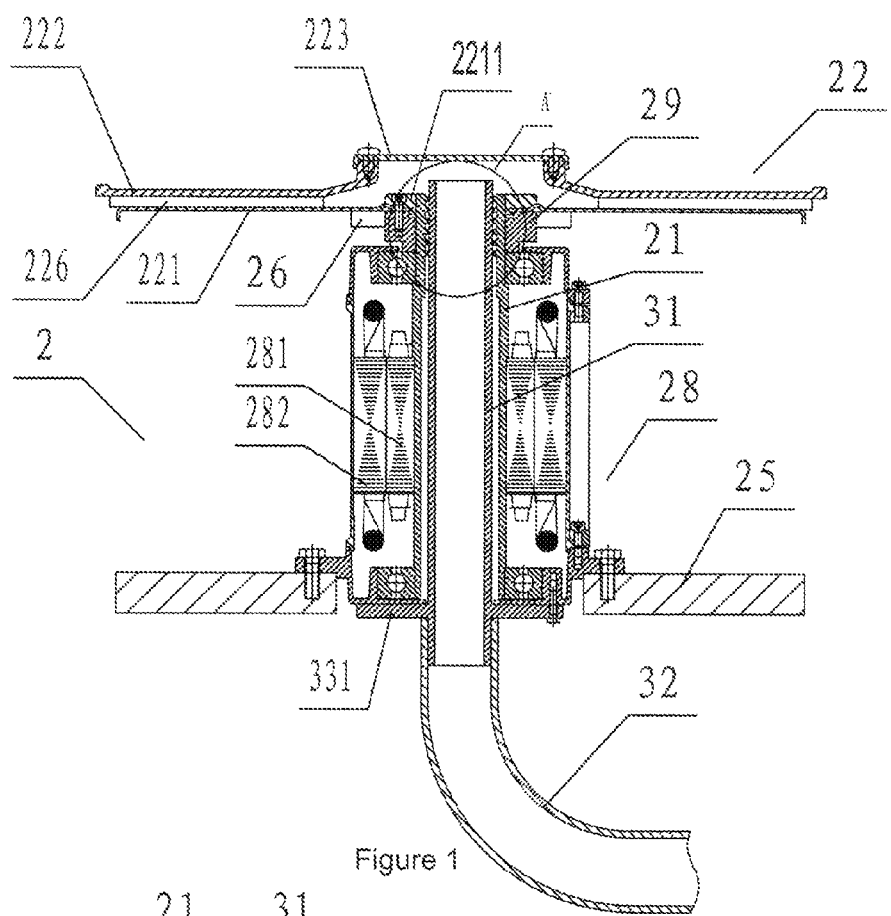
FIG. 1 is a perspective view of a feed-throwing mechanism of the present invention.
Figure 2:
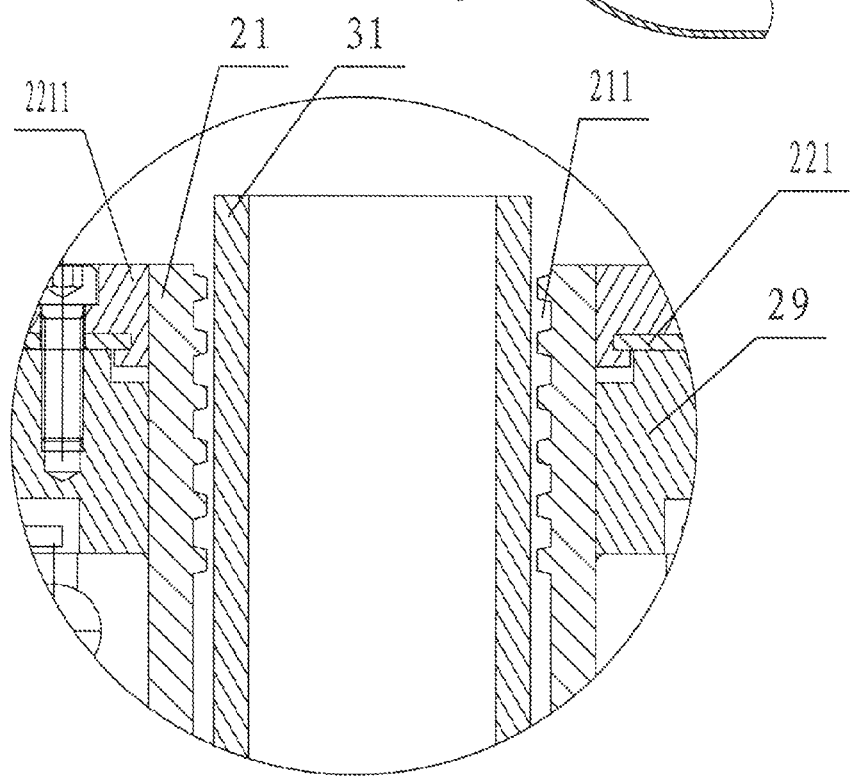
FIG. 2 is an enlarged view of a portion of the feed-throwing mechanism taken from A in FIG. 1 of the present invention.

REFERENCES feed-supplying mechanism 1
feed container 11 hopper 12
feed conveyer 13
discharge nozzle 14
injection-molded plate 111
cover 112
pin 113;
magnet pad 114
iron pad 115
connection plate 116
reinforcement bar 117
control device 119
filter 121
dustpan 131
rotatable door 132
feed electric motor 133
spindle of feed electric motor 134
eccentric sleeve 135
bearing 136
bearing support 137
rod 138
regulator 139
nut 140
end of the discharge nozzle 141
adjustment lever 142;
sidewall 1121
feed-throwing mechanism 2
hollow shaft 21
launching disc 22
gear transmission 23
rotor 24
base 25
fan 26
motor 28
flange 29
convex-concave structure 211
base 221
cover 222
closures 223
housing 224;
distributing tube 225
guide plate 226
guide channel 227
isolation plate 228
gear 231
pulley 232
belt 233
rotor 281
stator 282
mounting plate 2211
feed inlet 2212
the upper member of housing 2241
the lower part of housing 2242
the lower guide plate 2261
the upper guide plate 2262
feed-conveying mechanism 3
discharging pipe 31
conveying pipe 32
filter 33
suction pipe 34
valve 35
feed inlet 36
auger 37
air blower 38
flange 331
bank of fish ponds 4
water 5
stake 6
floating device 7
floating ball 71
supporting rod 72

DETAILED DESCRIPTION OF PREFERRED EMBODIMENT

Figure 5:
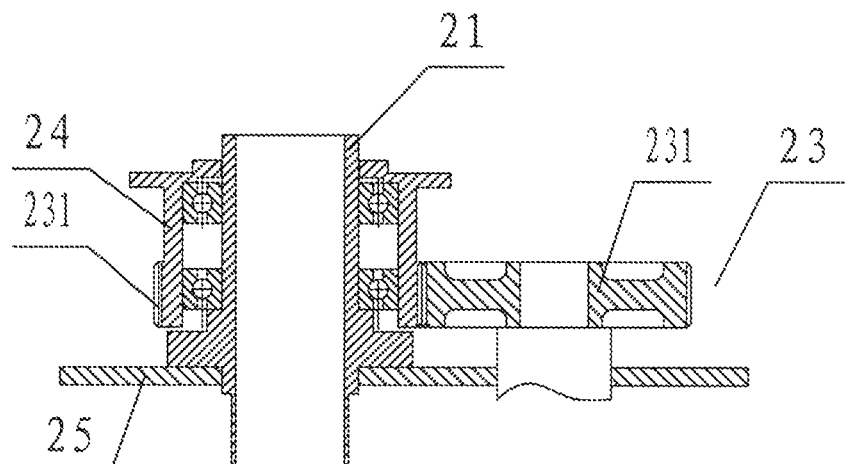
FIG. 5 is a perspective view of a gear transmission mechanism.
Figure 12:
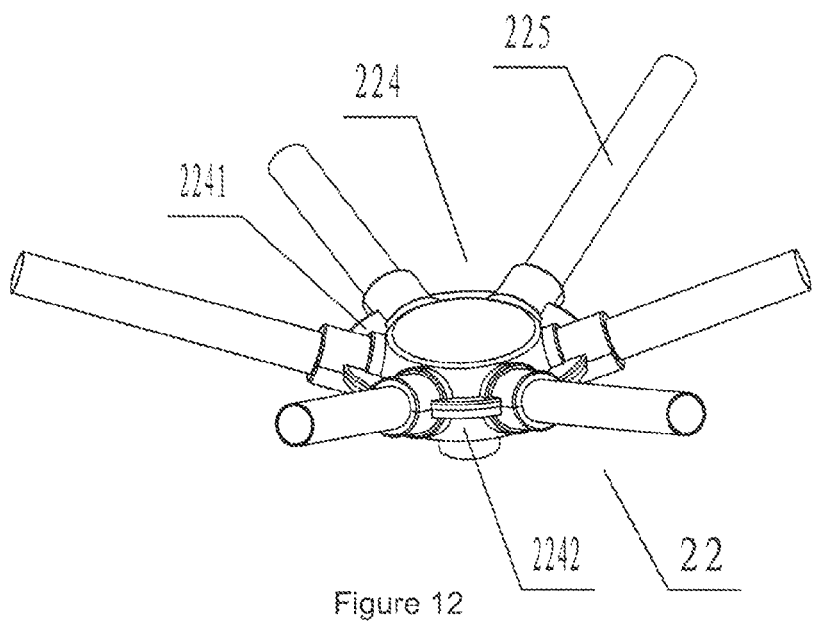
FIG. 12 is a three-dimensional view of a launching disc with distributing tubes.
Figure 25:
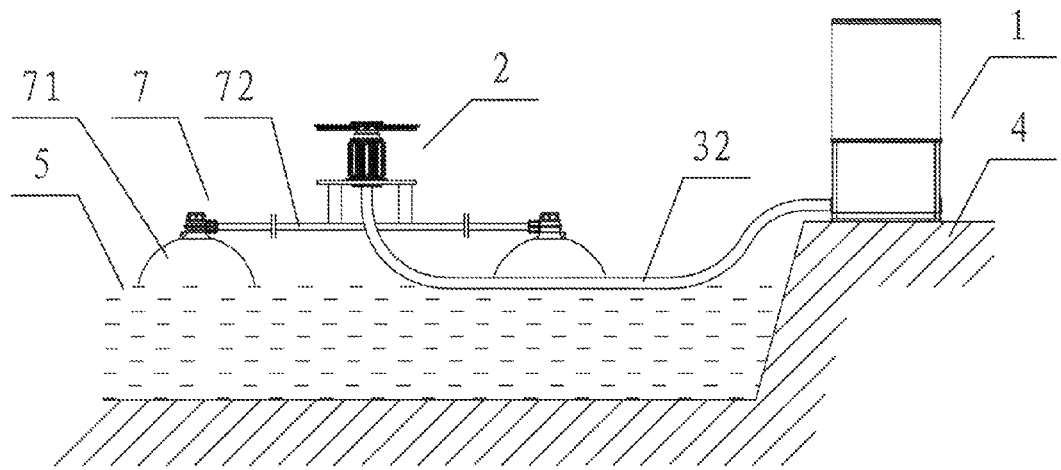
FIG. 25 is a perspective view of the feed-throwing mechanism floating on the water.

Referring first to FIG. 25, a feed distributor with feed supplied from below and thrown circumferentially comprises: a feed-supplying mechanism 1; a feed-throwing mechanism 2 for throwing feed from said feed-supplying mechanism 1, which has a launching disc 22 (FIG. 12) with a sealed top, feed outlets in its circumference and a feed inlet 2212 below (FIG. 8) and disposed on a hollow shaft 21 (FIG. 5) whose inner hole is opposed to said feed inlet 2212 below (FIG. 8); a feed-conveying mechanism 3 (FIGS. 13-15), by which feed supplied from said feed-supplying mechanism 1 is conveyed to said feed-throwing mechanism 2.

Figure 6:
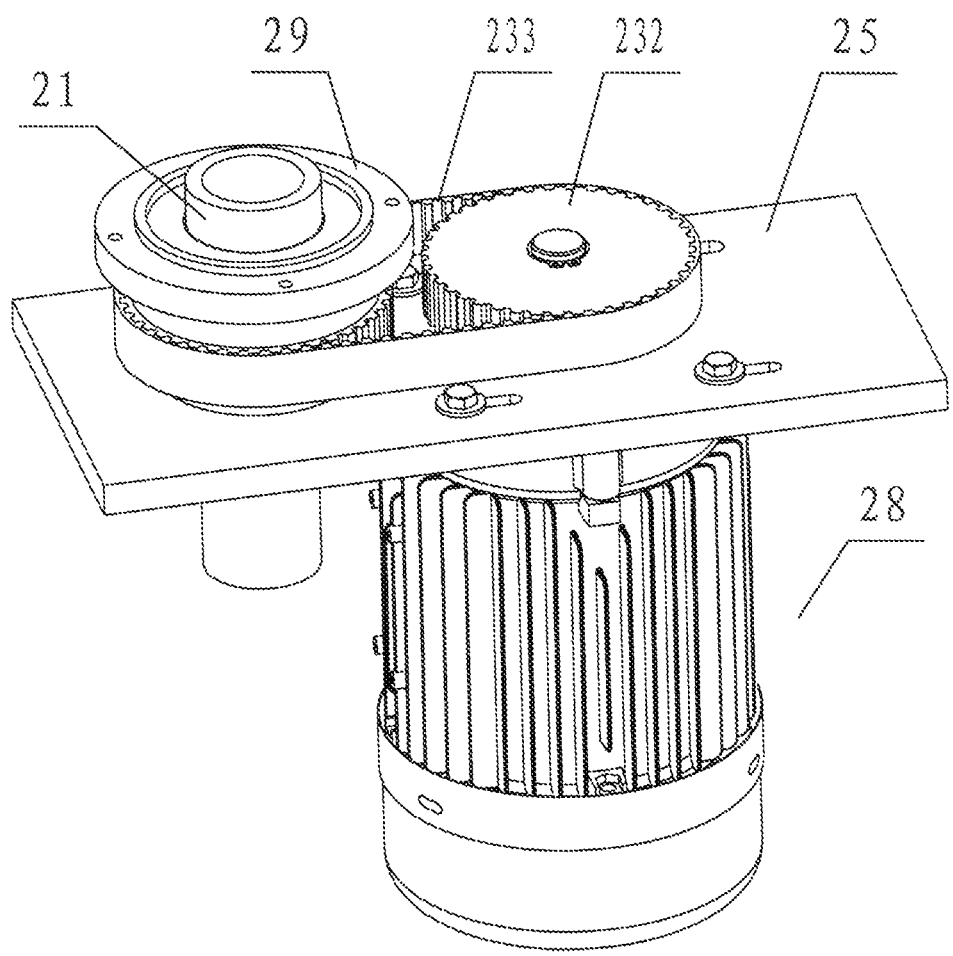
FIG. 6 is a perspective view of a belt transmission mechanism.

Referring to FIG. 1, said launching disc 22 rotates with said hollow shaft 21 by transmission means 23 (FIG. 5) when the power is on. Alternatively, said launching disc 22 can rotate by an electric motor with a hollow spindle which forms said hollow shaft 21. Still referring to FIG. 1, a discharge tube 31, which does not rotate, and connects with a conveying pipe 32 below is disposed in the inner hole of said hollow spindle, and said discharge tube 31 could be adjusted in altitude and disassembled or assembled freely. Alternatively, said hollow shaft 21 can be disposed fixedly on a base 25 for supporting a rotor with a bearing outside; and said rotor is driven with power by a transmission means. Alternatively, said rotor is the rotor from an electric motor with a hollow spindle which forms said hollow shaft 21; and said hollow spindle connects with a conveying pipe 32 below. Said transmission means 23 (FIG. 5) could be a kind of gear 231, or belt 232 (FIG. 6), and so on.

Sealing means is disposed between said discharge tube 31 and hollow shaft 21 to avoid feed or dust deposition. Alternatively, a circular or spiral convex-concave structure 211 can be disposed in the outer surface of said discharge tube 31 or inner surface of said hollow shaft 21 to avoid feed or dust deposition.

Figure 4:
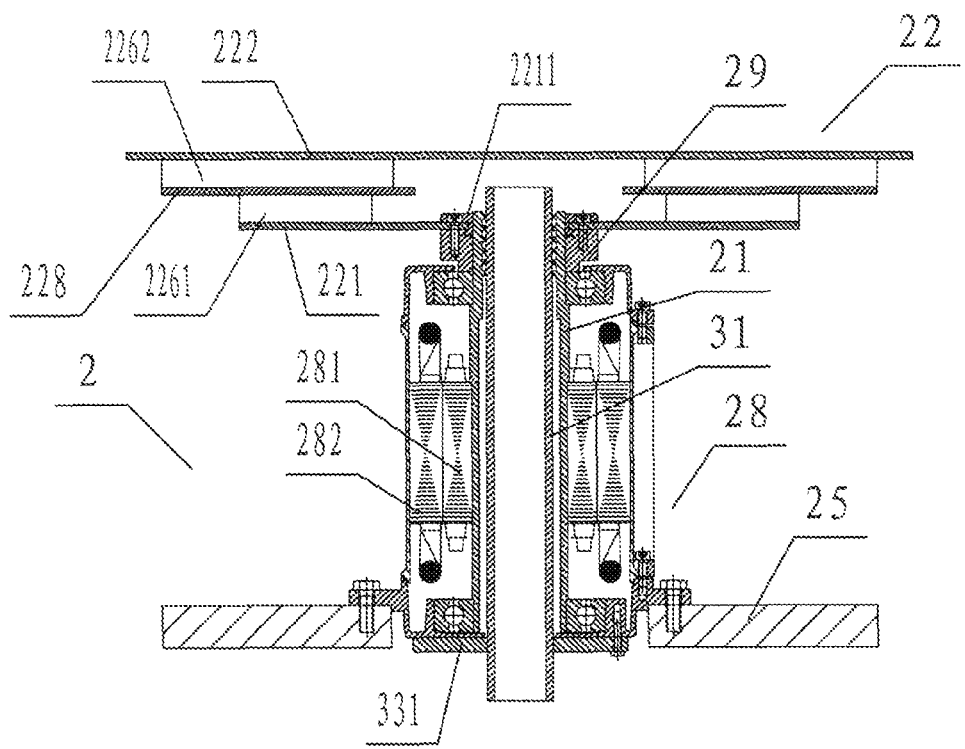
FIG. 4 is a perspective view of feed-throwing mechanism with an isolation plate in the launching disc.
Figure 7:
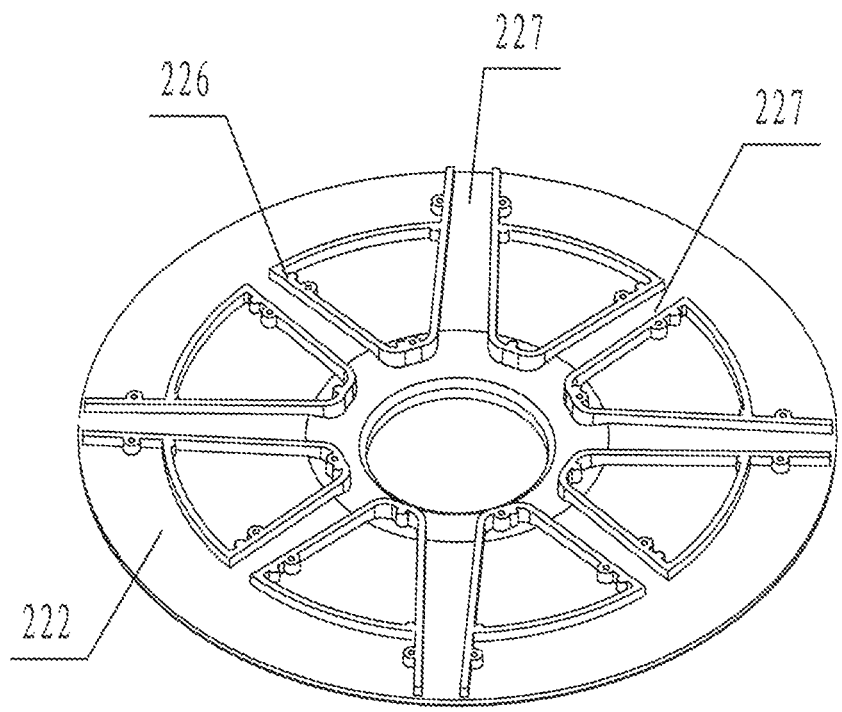
FIG. 7 is a perspective view of the upper member of a launching disc and guide plates in as a set.
Figure 8:
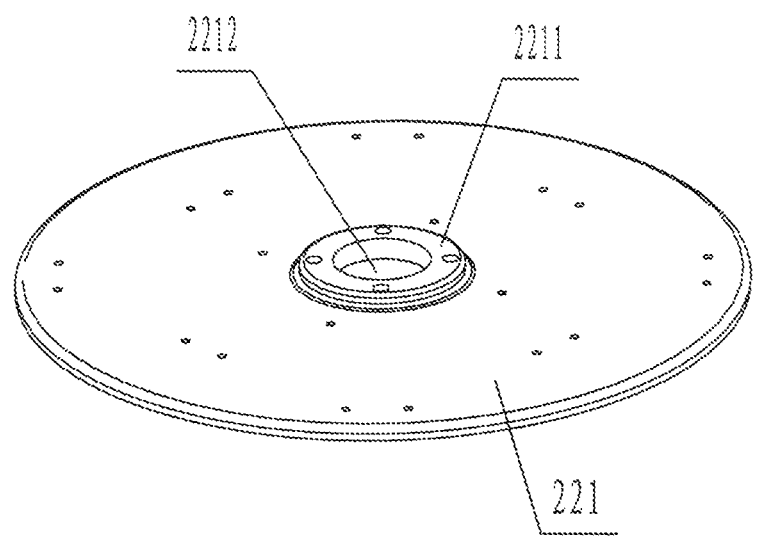
FIG. 8 is a perspective view of the lower part of the launching disc.
Figure 9:
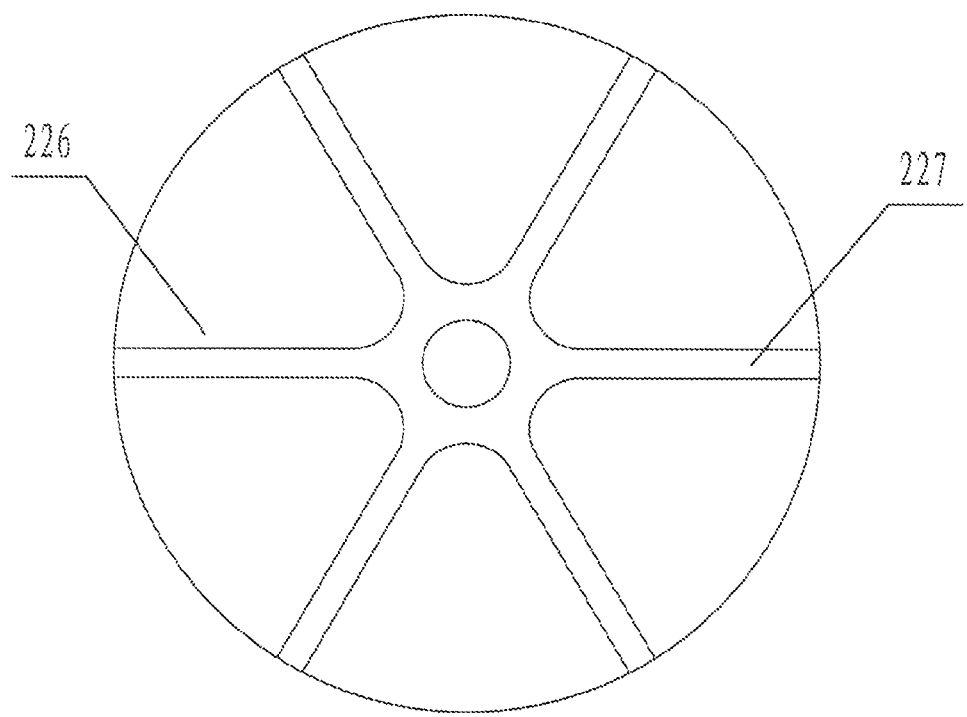
FIG. 9 is a perspective view of a guide channel of the balance type.
Figure 10:
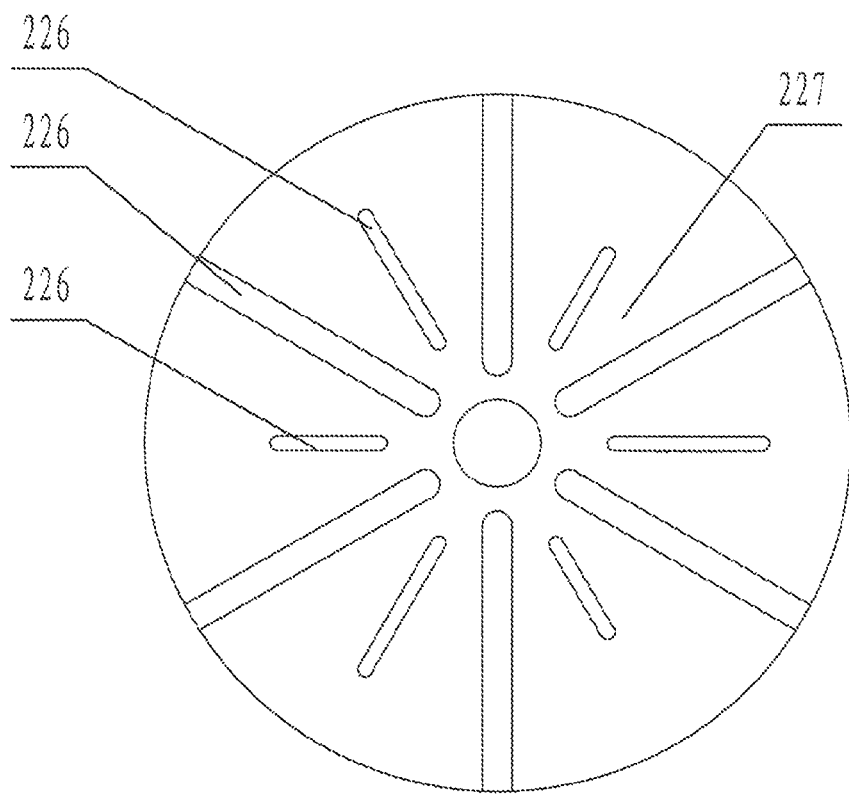
FIG. 10 is a perspective view of a guide channel of the diffusion type.
Figure 11:
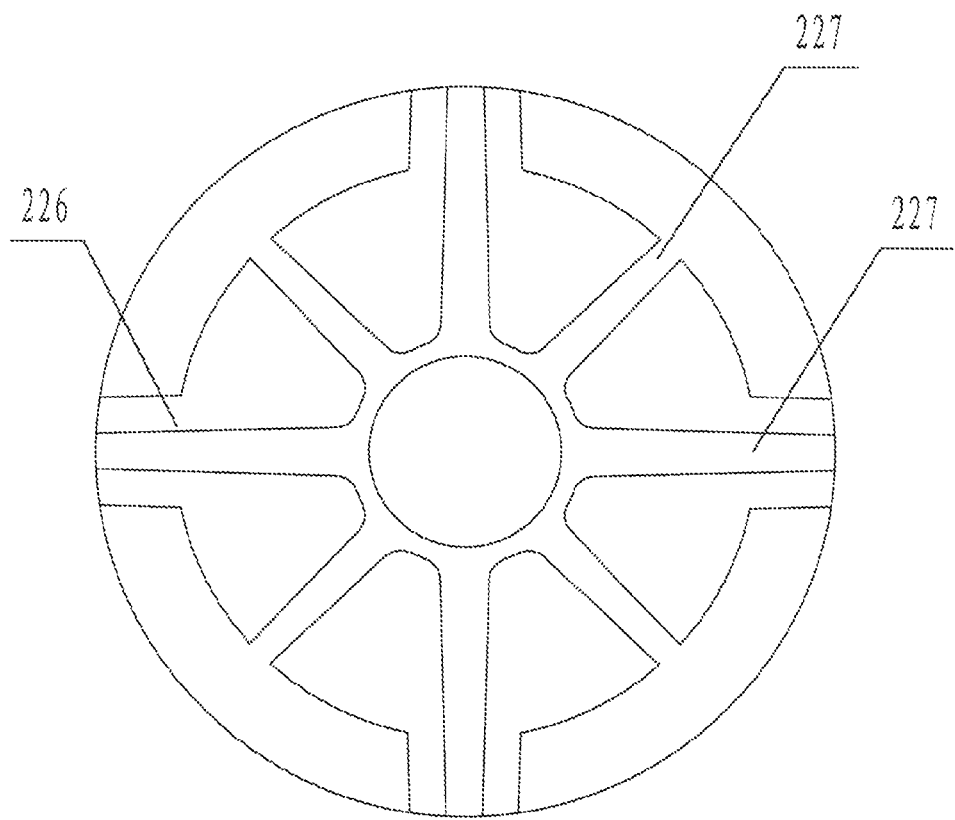
FIG. 11 is a perspective view of a guide channel of the contraction type.

Referring to FIGS. 4 and 8, said launching disc 22 could be composed of an upper member 222 and a lower member 221, and said lower member 221 has a mounting plate 2211 and said feed inlet 2212; between said lower member 221 and upper member 222, a linear or curved guide plate 226 for feed throwing is disposed evenly within the circumference of the lower and upper members in a radial direction outwards in line with a certain radius; a guide channel 227 (FIG. 7) is formed by cavities between two of said guide plates 226 which can be of a diffusion type (FIG. 10), with a big opening outside and smaller opening inside in the radial direction; a contraction type (FIG. 11), with a big opening inside and a smaller opening outside in the radial direction; or a balance type (FIG. 9), with the same size of openings outside and inside in the radial direction; said launching disc 22 can have a hollow case 224 with an upper member 2241 and a lower member 2242 which has a mounting position and said feed inlet 2212 underneath, and guide tubes 225 disposed along the circumference of the juncture between said upper member 2241 and lower member 2242, and said upper member 2241 and lower member 2242 could be made of plastic or aluminum subject to injection molding or die casting; said guide channels 227 or tubes 225 are disposed horizontally at the same level, or with the outside part a little higher than the inside part in the radial direction so that feed could be thrown in an elevated angle for a wider coverage, and/or in different lengths in the radial direction for an even distribution within said coverage; and the cross-section of said guide tubes 225 is rectangular, circular or any kind of curvature that reduces the air resistance (streamlined).

Figure 3:
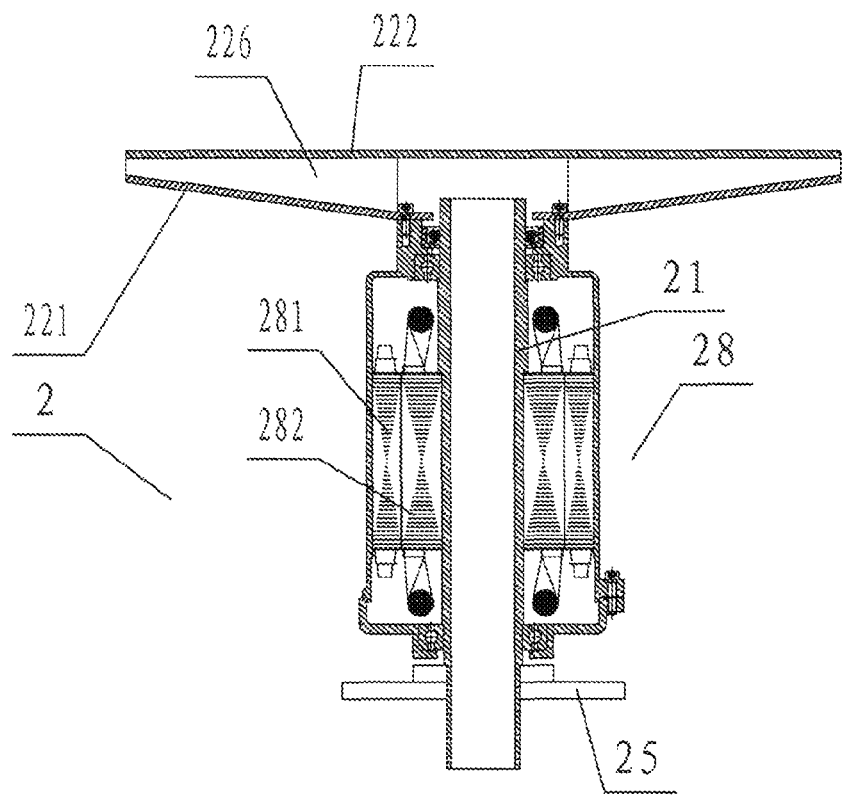
FIG. 3 is a perspective view of feed-throwing mechanism with an electric motor with a hollow spindle.

Referring to FIGS. 1 and 3, the lower member 221 of said launching disc 22 is a conical or flat revolver made from metal sheet or plate subject to metal extrusion, and the rim of said lower member 221 could face down as a reinforcement ring. In the center of said lower member 221, there is a ring-shaped mounting plate 2211 riveted with said lower member 221, and said lower member 221 is fixed to a flange 29 of said hollow shaft 21 with bolts in the countersunk of said ring; alternatively, said lower member 221 connects directly with the flange 29 of said hollow shaft 21. Other means could be used that could fix said lower member 221 horizontally on said vertical hollow shaft 21. It is understood in the art that the phrase "horizontally" or "vertical" means not absolutely but basically horizontally or vertical. As feed is thrown in an elevated angle at a certain speed, the feed locus is in the shape of parabola. A cooling fan 26 for said electric motor is disposed under said lower member 221 or flange 29; said upper member 222 and guide plates 226 could be a whole-set formed together by injection molding or die casting, or separate from each other; said upper member 222 is top-sealed and a little bigger on the outside diameter than said lower member 221 in case of rain; and said upper member 222 has an opening in its center for the convenience of assembly and disassembly, engaged with a sealed member 223.

Referring to FIGS. 9-12, said guide plates 226, channels 227 or tubes 225 of said launching disc 22 are disposed separately in different lengths in the radial direction; and/or, said guide channels 227 are separated by isolation plates 228 (FIG. 4) into an upper channel and a lower channel, in different length, and said isolation plates 228 and guide plates 226 are a whole-set made by injection molding or die casting. The proportional ratio of feed for said upper channel and lower channel could effectively be regulated or controlled with an adjustment of the height of said discharge tube 31 in said launching disc 22.

Figure 16:
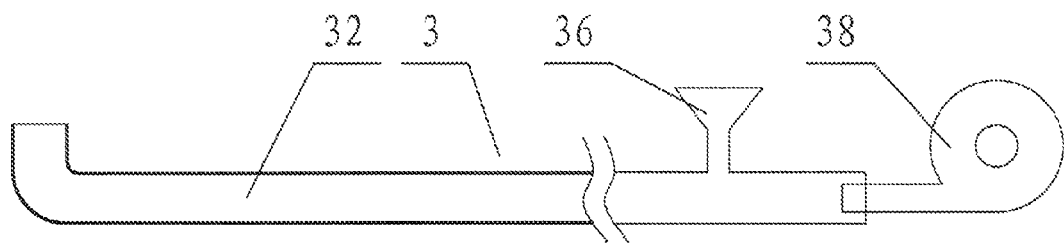
FIG. 16 is a perspective view of the fourth form of a feed-conveying mechanism
Figure 17:
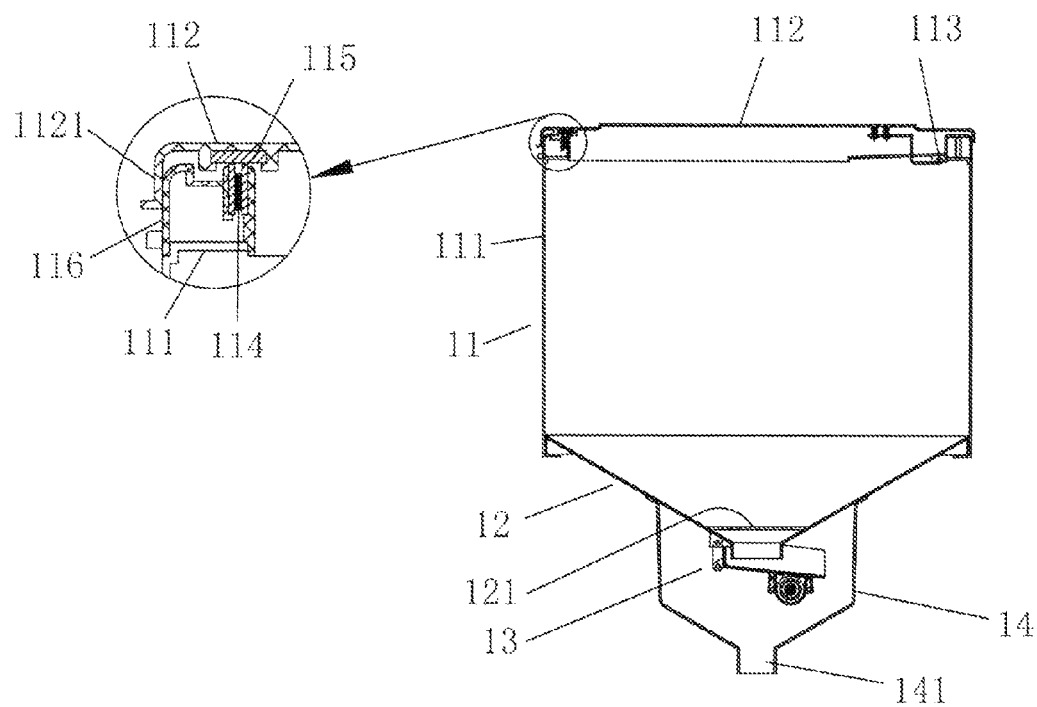
FIG. 17 is a perspective view of a feed-supplying mechanism.
Figure 22:
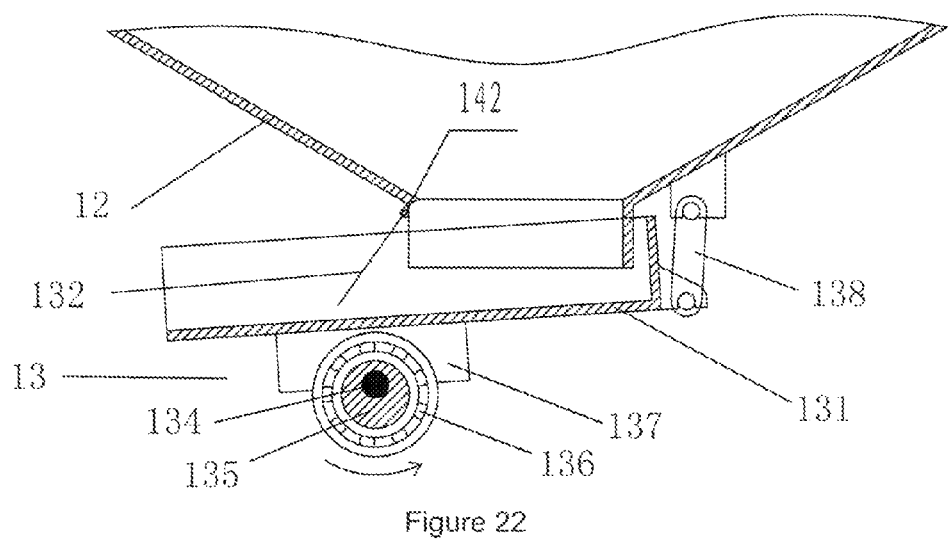
FIG. 22 is a perspective view of the dustpan of the feed conveyor in the lowest position.
Figure 23:
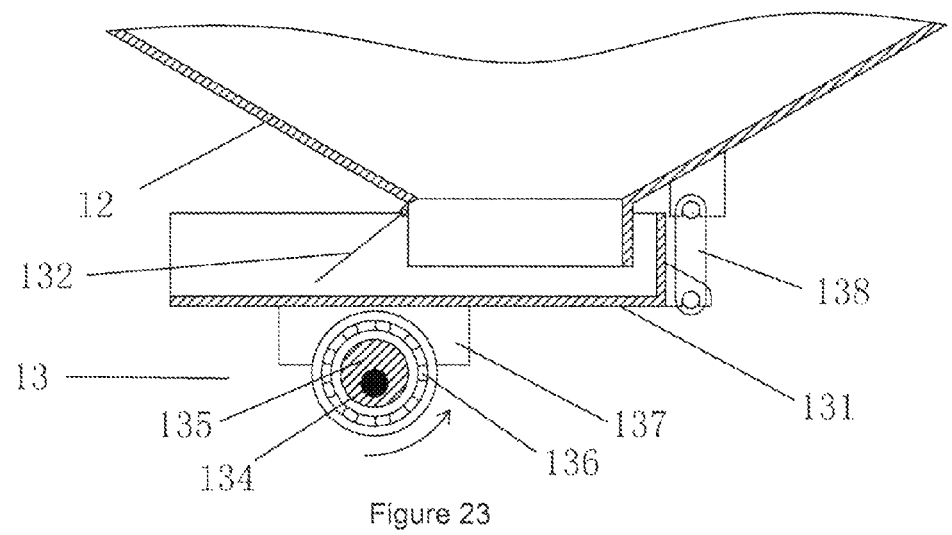
FIG. 23 is a perspective view of the dustpan of the feed conveyor in the highest position.

Referring to FIG. 17, the configuration of said feed-supplying mechanism 1 is as follows: a cone-shaped hopper 12 connects with a feed container 11 above and a feed conveyer 13 below, adjustable in feeding rate and interval time. The configuration of said feed conveyer 13 is as follows: said cone-shaped hopper 12 has a filter 121 inside and connects with a discharge nozzle 14 below, and a feed conveyor 13 disposed at the opening of said hopper 12 within said discharge nozzle 14. Referring to FIG. 22, the configuration of said feed conveyor 13 is as follows: a dustpan 131 couples to said opening of said hopper 12, and the back wall of said dustpan 131 pivots outwards with an end of a lever 138, and the other end of said lever 138 connects to the back wall of said hopper 12. A rotatable door 132 which could block said dustpan 131 pivots to the front wall of said hopper 12, and said rotatable door 132 has an adjusting lever 142 with a regulator 139 outside (FIG. 20), and said feeding rate could be adjusted by rotating of said regulator 139 fixed where needed in accordance with feeding rate by bolts 140 or the like. An eccentric sleeve 135 is disposed in the inner ring of a bearing 136 with a bearing support 137 at the bottom of said dustpan 131, and a feed electric motor whose spindle 134 connects with said eccentric sleeve 135 mounts fixedly below said hopper 12, and said discharge nozzle 14 (FIG. 20) connects with charge opening 36 (FIGS. 13-16) of said feed-conveying mechanism 3. Alternatively, referring to FIGS. 17 and 15, the configuration of said feed conveyer 13 can be as follows: said cone-shaped hopper 12 connects with a discharge nozzle 14 below, and the very end 141 of said discharge nozzle 141 connects with charge opening 36 of said feed conveying mechanism 3 with an auger 37 used for regulation of said feeding rate.

Figure 13:
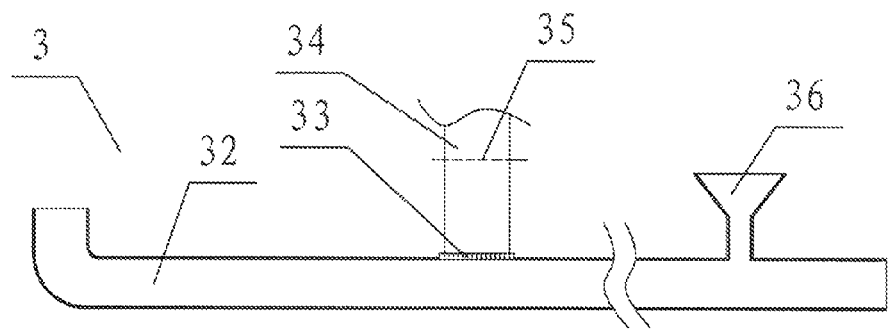
FIG. 13 is a perspective view of the first form of feed-conveying mechanism.
Figure 14:
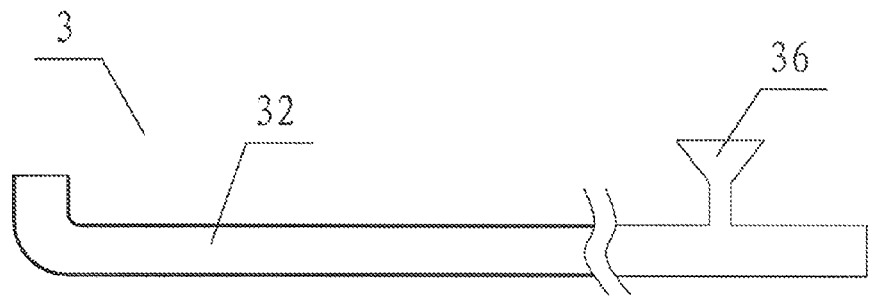
FIG. 14 is a perspective view of the second form of a feed-conveying mechanism.
Figure 15:
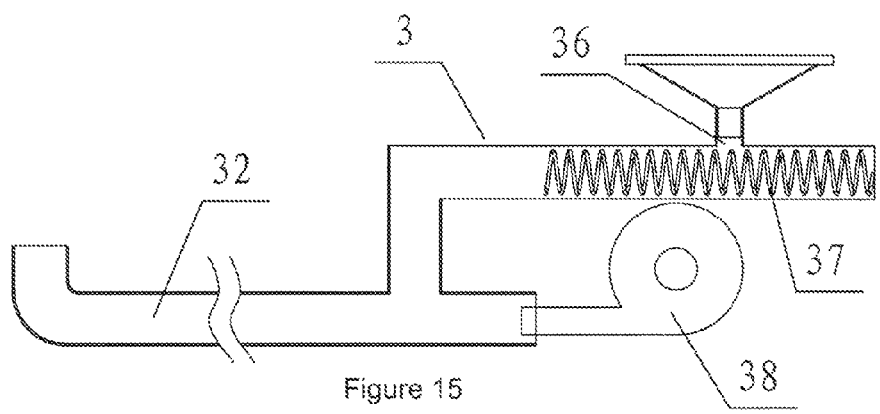
FIG. 15 is a perspective view of the third form of a feed-conveying mechanism.

Said feed-conveying mechanism 3 comprises only a conveying pipe 32 which connects with said feed-supplying mechanism 1 in one end and said feed-throwing mechanism 2 in the other as shown in FIG. 14. In the event the negative pressure generated by rotation of said launching disc 22 is not enough for long distance feed throwing, a suction device with a filter 33 and valve 35 is disposed in the middle of the conveying pipe 32 and interacts with the conveying pipe as shown in FIG. 13. Under the action of said suction device and launching disc 22, feed is sucked into said conveying pipe 32 but not into the tube 34 of said suction device as a result of said filter 33. Said valve 35 could be used to regulate air flow in the tube 34 or make said suction device work intermittently. Alternatively, an air blower 38 can be disposed at the end of, and outside of, said conveying pipe 32, in the direction from the charge opening 36 to the discharge opening, as shown in FIG. 16. Alternatively, an auger 37 for propelling feed forward can be disposed at the end of said conveying pipe 32 where said charge opening 36 lies as shown in FIG. 15, and an air blower 38 can be disposed somewhere outside of said conveying pipe 32 to facilitate forward movement of feed.

Said conveying pipe 32 is made from soft, transparent rubber pipe with a frame, connecting with said feed-supplying mechanism 1 at one end and a feed-throwing mechanism 2 at the other end. A discharge opening connects with said hollow shaft 21 or said discharge tube 31 and its central part floats in the water.

Figure 18:
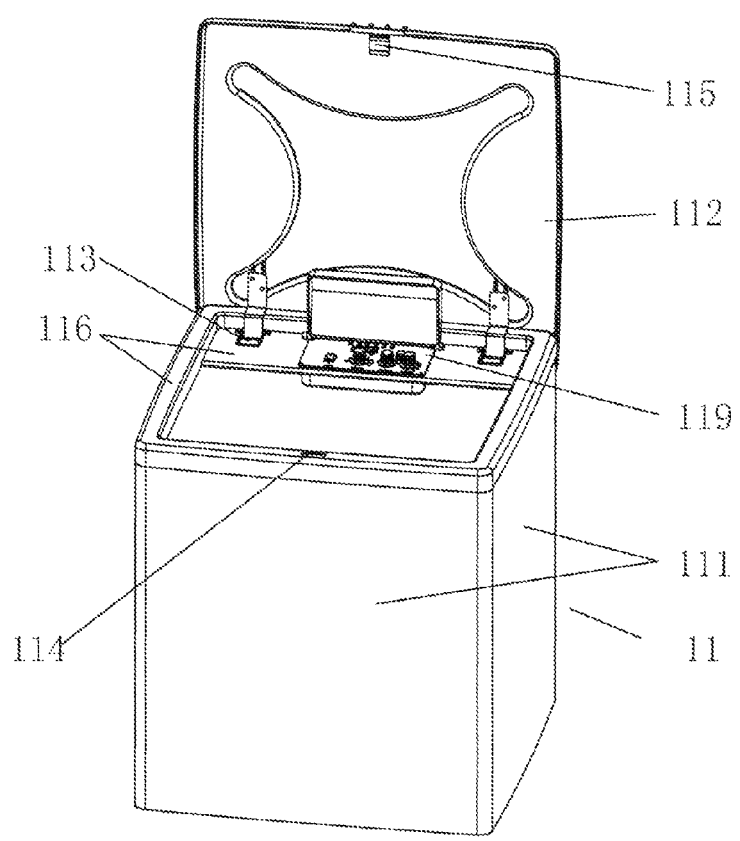
FIG. 18 is a three-dimensional view of a feed container and its control device.
Figure 19:
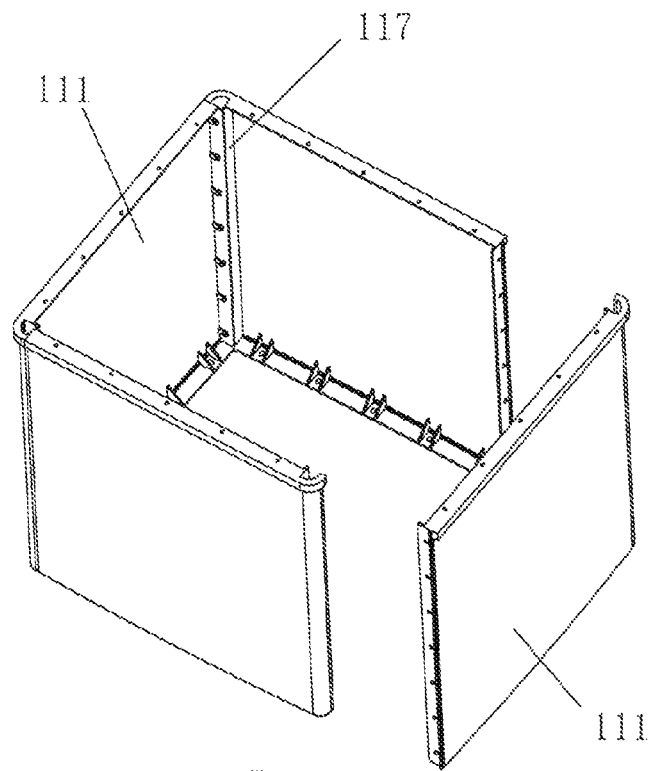
FIG. 19 is a three-dimensional view of a feed container with four combined injection-molded plates.
Figure 20:
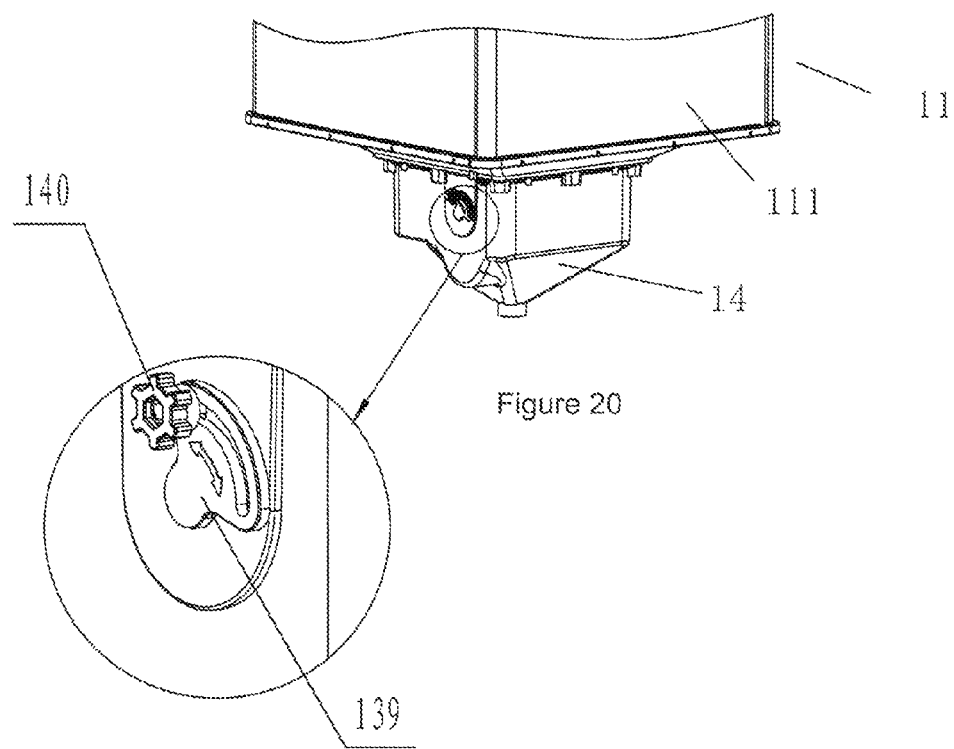
FIG. 20 is a three-dimensional view of an adjusting device.
Figure 21:
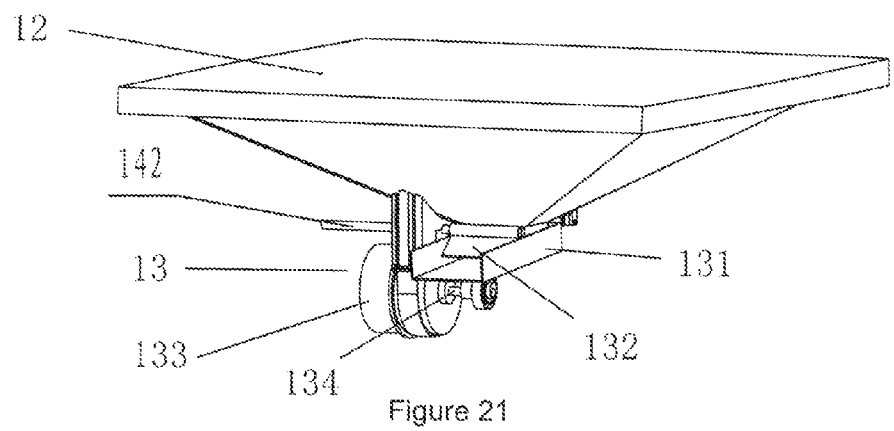
FIG. 21 is a three-dimensional view of the hopper and feed conveyor.

In reference to FIG. 18, FIG. 19 and FIG. 20, in the form of a barrel, said feed container 11 is combined in sequence with four identical injection-molded plates 111. Each of said plates 111 has a reinforcement bar 117 at a side which forms a reinforcement pillar in the corner when said plates 111 are combined together. On every top of said plates 111, there is a window frame-shaped connection board 116. The side walls 1121 of the cover 112 for said feed container 11 face inwardly against the side plates 111 of said feed container 11 correspondingly, and one of said side walls 1121 pivots with the corresponding side plates 111 of said container 11, and in the opposite side, the side wall 1121 of said cover 112 and side plate 111 of said feed container 11 are equipped with an iron or magnet pad correspondingly engaged to lock said cover 112. Continuous or intermittent performance of feed distribution could be controlled automatically by a controlling device 119.

Figure 24:
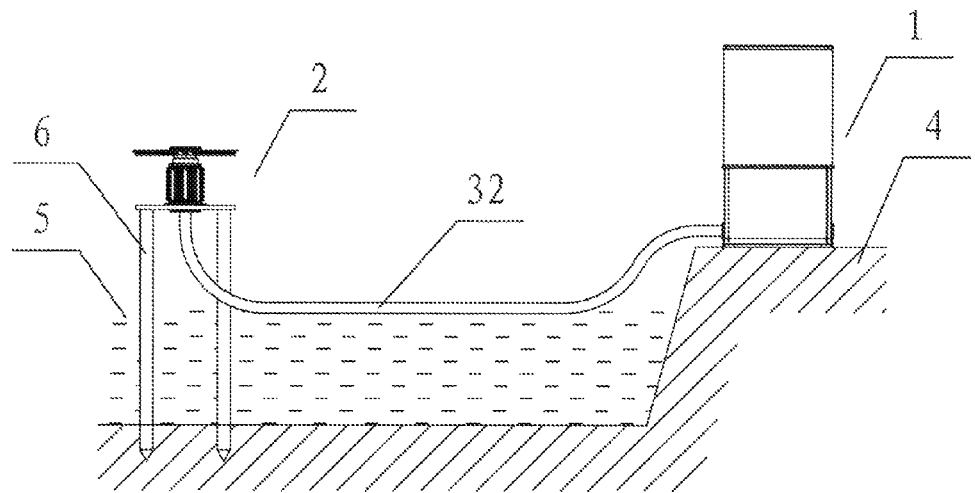
FIG. 24 is a perspective view of the feed-throwing mechanism supported by a stake in the water.

Referring to FIGS. 24 and 25, said feed-throwing mechanism 2 has a support below, and the support could be a floater 7, one or more stakes 6 fixed downwardly in the water, or a cement base, and so on. Said stakes 6 could be a steel pipe with one end welded to the base 25 (FIG. 5) of said feed-throwing mechanism 2 and the other end inserted into the ground under the water. Said floater 7 comprises three or four floating balls 71 around said feed-throwing mechanism 2 evenly, and the floating balls 71 connects fixedly with the base 25 of said feed-throwing mechanism 2 by supporting levers 72 which fix on the top of the balls 71.

In a word, the purpose of the support is to fix said feed-throwing mechanism 2 firmly in the water, therefore, support in any configuration or material such as cement and wood will do.

The invention is applied as follows: fix the feed-throwing mechanism 2 of the invention to a support in the water of a fish pond, and the feed-supplying mechanism 1 of the invention on a bank 4; connect the charge opening 36 of the feed-conveying mechanism 3 of the invention with the end 141 of the discharge nozzle 14 of said feed-supplying mechanism 1, or the discharge opening of the cone-shaped hopper 12, and connect the feed-conveying mechanism 3 with the feed-throwing mechanism 2; pour feed into the feed container 11; set up the feed throwing time or interval time with the control device 119; with the power on, the electric motor for throwing the feed of the feed-throwing mechanism 2 and the other feed electric motor 133 for propelling feed forward of the feed-conveying mechanism 2 start to work in sequence; the dustpan 131 is actuated by the electric motor of the feed conveyer 13 of the feed-supplying mechanism 1 and vibrates horizontally and vertically, and pushes the feed forward. Under the action of gravity, the vibration from the dustpan 132, and the negative pressure from the rotation of the launching disc 22, feed is sucked into the launching disc 22 and thrown circumferentially and evenly into the water in a locus of parabola along the guide channels 227 or tubes 225 under the centrifugal force generated by rotation of the launching disc 22. Feed thrown is not blocked, which leads to a low crushing rate. The guide plates 226 or tubes 225 are different in length, and a longer one and a shorter one is disposed separately in a circumferential direction, which leads to an even distribution in the coverage area that can be adjusted by the rotating speed of the launching disc 22. Feed can be added into said feed container 11 at any time during throwing. An auxiliary feed conveyer can be used for supplying feed directly from a warehouse.

Although the preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

What is claimed:

1. A feed distributor used in fish ponds with feed supplied from below and thrown circumferentially comprises: a feed-supply mechanism; a feed-throwing mechanism; a feed-conveying mechanism by which feed supplied from said feed-supply mechanism is delivered to said feed-throwing mechanism; said feed-throwing mechanism has a launching disc with a sealed top, feed outlet along the circumference of said launching disc and a feed inlet below; said launching disc is disposed on a hollow shaft with an inner hole opposed to said feed inlet, wherein said feed-supplying mechanism has a cone-shaped hopper which connects with a feed container above and a feed conveyer below, adjustable in feeding rate and interval time; side walls of a cover for said feed container engage with the side plates of said feed container correspondingly, and one of said side walls pivots with one of said side plates of said container and an opposite side wall is equipped with an iron or magnet pad which engages correspondingly with an magnet or iron pad in the side plate of said container to lock said cover;

the configuration of said feed conveyer is as follows:
said cone-shaped hopper connects with a discharge nozzle below, and a feed conveyor is disposed at a bottom opening of said hopper within said discharge nozzle; said feed conveyor has a dustpan coupled to a lower part of said opening; a back wall of said dustpan pivots outwards with an end of a lever, and another end of said lever connects with the back wall of said hopper; a bearing with an eccentric sleeve mounted in its inner ring settles on a bearing support in the bottom of said dustpan, and a feed electric motor whose spindle connects with said eccentric sleeve mounts fixedly below said hopper, and said discharge nozzle connects with charge opening of said feed-conveying mechanism;
or, said cone-shaped hopper connects with a discharge nozzle below, and an end of said discharge nozzle connects with a charge opening of said feed-conveying mechanism; and,
a configuration of adjustment in feeding rate of said feed conveyer is as follows: a rotatable door which could block said dustpan pivots to a front wall of said hopper, and said rotatable door has an adjusting lever with a regulator outside, and said feeding rate is adjusted by rotation of said regulator fixed anywhere as needed by bolts.

* * * * *